United States Patent
Alibakhsh et al.

(10) Patent No.: US 9,304,761 B2
(45) Date of Patent: Apr. 5, 2016

(54) SYSTEM AND METHOD FOR COLLABORATIVE PROGRAMMING OF DATA ENTRY WORKFLOWS BETWEEN SYSTEM DEVELOPERS, END USERS, AND THIRD PARTY DEVELOPERS

(71) Applicant: Nuesoft Technologies, Inc., Marietta, GA (US)

(72) Inventors: Massoud Alibakhsh, Atlanta, GA (US); Shahram Famorzadeh, Marietta, GA (US)

(*) Notice: Subject to any disclaimer, the term of this patent is extended or adjusted under 35 U.S.C. 154(b) by 7 days.

(21) Appl. No.: 13/915,746

(22) Filed: Jun. 12, 2013

(65) Prior Publication Data
US 2014/0372965 A1    Dec. 18, 2014

(51) Int. Cl.
G06F 9/44     (2006.01)
G06F 9/45     (2006.01)
G06Q 10/06    (2012.01)

(52) U.S. Cl.
CPC .. G06F 8/70 (2013.01); G06F 8/71 (2013.01); G06Q 10/06 (2013.01); G06F 8/20 (2013.01); G06F 8/443 (2013.01); G06F 8/4441 (2013.01)

(58) Field of Classification Search
CPC ............ G06F 8/20; G06F 8/71; G06F 8/443; G06F 8/4441; G06F 8/44
See application file for complete search history.

(56) References Cited

U.S. PATENT DOCUMENTS

| | | | |
|---|---|---|---|
| 5,319,543 A | 6/1994 | Wilhelm | |
| 5,682,526 A | 10/1997 | Smokoff | |
| 6,551,243 B2 | 4/2003 | Bocionek | |
| 6,904,161 B1 | 6/2005 | Becker | |
| 7,051,071 B2* | 5/2006 | Stewart et al. | 717/136 |
| 7,371,068 B2 | 5/2008 | Lloyd | |
| 7,443,303 B2 | 10/2008 | Spear | |
| 7,653,634 B2 | 1/2010 | Mathur | |
| 7,660,416 B1* | 2/2010 | Kline | 715/723 |
| 7,930,268 B2 | 4/2011 | Starkey | |

(Continued)

OTHER PUBLICATIONS

Minch et al. "Integrating the HIE into the EHR Workflow", Jul. 2011, HIMSS 2010-2011 Health Information Exchange Committee, HIE Provider Engagement Workgroup, pp. 1-11; <http://himss.files.cms-plus.com/2011-08-08-IntegratingtheHIEintotheEHRWorkflow.pdf>.*

(Continued)

*Primary Examiner* — Thuy Dao
*Assistant Examiner* — Ben C Wang
(74) *Attorney, Agent, or Firm* — Mathew L. Grell; Grell & Watson Patent Attorneys

(57) ABSTRACT

The present invention is a system for collaborative programming of data entry workflows between end users, Electronic Health Record (EHR) system developers, and third party developers. The system comprises application servers, database servers, an EHR, networked devices, and peripheral devices, all stored in a distributed computing environment. The database servers comprise databases, which host workflows programmed by end users, EHR developers, and third party developers. The system also has a secure network connection for data exchange between application and database servers, and networked devices. The EHR gathers patient health information, processes it and stores it in one of the databases. The system itself, stored in one of the application servers, uses a plurality of templates (form, system and external system) stored in one of the databases to interact with the peripheral devices connected to networked devices that expand the capabilities of the networked devices or the EHR itself.

13 Claims, 6 Drawing Sheets

(56) References Cited

U.S. PATENT DOCUMENTS

| | | |
|---|---|---|
| 8,050,938 B1 | 11/2011 | Green, Jr. |
| 8,103,906 B1* | 1/2012 | Alibakhsh et al. .............. 714/13 |
| 8,719,174 B2* | 5/2014 | Peters et al. ................. 705/310 |
| 2004/0039848 A1* | 2/2004 | Estrada et al. ................ 709/315 |
| 2004/0187140 A1* | 9/2004 | Aigner et al. ................ 719/328 |
| 2005/0137912 A1 | 6/2005 | Rao |
| 2005/0144232 A1* | 6/2005 | Estrada et al. ................ 709/204 |
| 2005/0289532 A1* | 12/2005 | Zakon et al. ................. 717/165 |
| 2006/0236301 A1* | 10/2006 | Minium et al. ............... 717/101 |
| 2006/0271390 A1* | 11/2006 | Rich et al. ......................... 705/1 |
| 2007/0089047 A1* | 4/2007 | Joshi ........................ 715/501.1 |
| 2010/0179852 A1* | 7/2010 | Tomizuka et al. ................ 705/9 |
| 2011/0099027 A1* | 4/2011 | Weathers .......................... 705/2 |
| 2012/0084598 A1* | 4/2012 | Alibakhsh et al. ........... 714/4.11 |
| 2012/0101843 A1* | 4/2012 | Mathur et al. ..................... 705/2 |
| 2012/0316890 A1* | 12/2012 | Mullin et al. ..................... 705/2 |
| 2013/0041677 A1* | 2/2013 | Nusimow et al. ................ 705/2 |
| 2013/0085798 A1* | 4/2013 | Spatola et al. ............... 705/7.24 |
| 2013/0144566 A1* | 6/2013 | De Biswas ........................ 703/1 |
| 2013/0191161 A1* | 7/2013 | Churchwell et al. ............. 705/3 |
| 2014/0100882 A1* | 4/2014 | Hamilton et al. ................. 705/3 |
| 2014/0188458 A1* | 7/2014 | Alibakhsh et al. ................ 704/9 |
| 2014/0207486 A1* | 7/2014 | Carty et al. ....................... 705/2 |
| 2014/0259105 A1* | 9/2014 | Alibakhsh et al. ............... 726/3 |
| 2014/0278471 A1* | 9/2014 | Alibakhsh et al. ............... 705/2 |

OTHER PUBLICATIONS

Ben-Tzion Karsh, "Clinical Practice Improvement and Redesign: How Change in Workflow Can Be Supported by Clinical Decision Support", Jun. 2008, University of Wisconsin—Madison, pp. 1-43; <http://www.nachc.com/client/Clinical%20Practice%20Improvement%20and%20Redesign_How%20Workflow%20can%20Support%20CDS.pdf>.*

Nemeth et al., "The Messy Details: Insights From the Study of Technical Work in Healthcare", 2004 IEEE, pp. 689-692; <http://ieeexplore.ieee.org/stamp/stamp.jsp?tp=&arnumber=1344116>.*

Sachdeva et al., "Semantic Interoperability in Standardized Electronic Health Record Databases", Apr. 2012, ACM, pp. 1:1-1:37; <http://dl.acm.org/results.cfm?h=1&cfid=559694347&cftoken=95322267>.*

* cited by examiner

TEMPLATE/WORKFLOW CREATION

EXEMPLARY USER INTERFACE ON DISPLAY DEVICE

EXTERNAL SYSTEM TEMPLATE DIAGRAM

VENDOR DATA GOING THROUGH API

API DIAGRAM

EXEMPLARY INSERTION OF ELEMENTS INTO WORKFLOWS BASED ON LOGIC

SYSTEM AND METHOD FOR COLLABORATIVE PROGRAMMING OF DATA ENTRY WORKFLOWS BETWEEN SYSTEM DEVELOPERS, END USERS, AND THIRD PARTY DEVELOPERS

CROSS-REFERENCE TO RELATED APPLICATIONS

None

FEDERALLY SPONSORED RESEARCH OR DEVELOPMENT

None

PARTIES TO A JOINT RESEARCH AGREEMENT

None

REFERENCE TO A SEQUENCE LISTING

None

BACKGROUND OF THE INVENTION

1. Technical Field of the Invention

The present invention relates generally to data entry and processing. Specifically, it provides a system and method for collaborative programming of data entry workflows between end users, system developers, and third party developers.

This method can be applied to any domain where record keeping is required. However, it will be of greatest benefit to the field of healthcare.

2. Description of Related Art

Current healthcare regulations require medical providers to collect complete and accurate patient information during encounters. Collected data is used in diagnosis, treatment, insurance claims, and pandemic reporting. Failure to document the unique needs of each patient could result in legal consequences or loss of life.

In order to comply with regulations, providers adopted Electronic Health Record (EHR) or Electronic Medical Record (EMR) systems to track patient information. The core of EHR/EMR systems comprise sequentially structured forms known as workflows, which allow providers to capture health information (e.g., heart rate, blood pressure, weight, etc. . . . ) during patient encounters. In order to meet the unique and changing needs of patients, providers must constantly create and modify workflows.

Prior art patents and other publications offer several attempts to meet these challenges. For example, in a plurality of EHR/EMR systems, software developers code new workflows and modify existing workflows. As a result, providers must plan the "business logic," submit a new workflow or workflow change request, and follow an extensive revision and implementation cycle. This approach is inefficient and costly due to protracted back-and-forth communication between providers and software developers.

Other EHR/EMR systems attempt to reduce the need for new workflows by adding free notation features that capture unstructured patient information. The resulting data requires a technician to manually code it into structured format, thereby increasing inaccuracy due to human error.

Some prior art systems try to remedy the need for having system developers manually code workflows by allowing providers to create structured data fields. However, the large number of fields makes capturing data cumbersome. Furthermore, providers must constantly manage fields to prevent redundancy and data corruption.

Other prior systems describe methods of creating or modifying workflows to interface with third party peripheral devices, so that data field values are automatically entered into workflows. Unfortunately, current technology requires system developers to alter EHR/EMR software each time the software must accommodate a new peripheral device. One skilled in the art would recognize this process as tedious and time-consuming.

At least one system attempts to improve peripheral device integration by incorporating proprietary medical imaging machine interfaces into workflows. Differences among proprietary imaging device interfaces result in a lack of uniformity in terminology, navigation, and features. This lack of uniformity places an unnecessary burden on providers to learn the proprietary interface of each imaging device in order to use them effectively. The lack of uniformity also increases human error in patient data collection.

The above mentioned solutions, as well as others, are narrowly focused and inadequate for providing an efficient and effective means for creating and modifying workflows. Therefore, it is readily apparent that there is a need for a system and method that allows collaborative programming of data entry workflows between end users, system developers, and third party developers.

BRIEF SUMMARY OF THE INVENTION

Briefly described, in a preferred embodiment, the present invention overcomes the above-mentioned disadvantages and meets the recognized need for such a device by providing a system and method for collaborative programming of data entry workflows between system developers, end users, and third party developers.

In the preferred embodiment, collaborative programming is achieved via the creation, modification, and arrangement of templates and workflows by system developers, end users, and third party developers through the EHR/EMR.

The EHR/EMR comprises at least one server, which comprises at least one application server, at least one database server, at least one template, and at least one workflow. End users can directly and independently build new templates and workflows with a networked device over a secure network connection or modify those that are already in use.

Generally speaking, system developers build and maintain the EHR/EMR. Conversely, third party developers create peripheral devices and/or external systems that interface with the EHR/EMR. In most cases, end users are medical providers including but not limited to physicians, physician assistants, and nurse practitioners.

The EMR/EHR collects all patient data gathered during a patient encounter (e.g., provider notes, imaging, lab work, vital signs) with at least one workflow comprised of at least one sequentially ordered template. Three template types are used to meet the needs of end users: form templates, system templates, and external system templates. Each template integrates unique functionality into workflows.

Form templates capture structured patient information with data fields (e.g., combo boxes, text boxes, list boxes, radio buttons, and check boxes). System developers create a plurality of default form templates to address the most common needs of end users. If needed, end users can create new form templates or modify existing form templates to meet their unique needs in a simple WYSIWYG (what you see is what you get) environment.

System templates provide more advanced functionality by capturing and processing information. System templates are built by system developers. End users input information into system templates in order to access advanced functionality built into the EHR/EMR. Processed information can be stored as structured patient information. In one embodiment, a system template searches for and schedules the next available appointment at a specified time with a specified provider.

External system templates provide complete integration with external devices and systems. Proprietary APIs (application programming interfaces) supply the framework for third party developers to seamlessly integrate external device functions into new and existing workflows. Each device function can be used independently when a specified condition is met. All types of users can specify said conditions.

Another feature of external system templates is interface uniformity. Prior art teaches systems where complex third party interfaces are displayed in windows. End users must select the proper functions of the peripheral device. The present invention allows third party developers to create situation-specific external system templates that only display the required peripheral functions.

In one embodiment, an end user is presented with an X-Ray machine external system template after diagnosing a patient with a broken arm. The external system template has default settings for scanning a broken arm and is ready to initiate a scan with the push of a button. Scan setting defaults are based on the diagnoses or can be manually altered during patient encounters.

Templates are arranged into default workflows by system developers, third party developers, and end users. Workflows are automatically chosen for end users based on the chief complaint collected during check-in. Unlike previous systems, end users can modify workflows during patient encounters by manually inserting templates or inactive workflows without leaving the active workflow.

Templates and inactive workflows can also be automatically injected into active workflows based on symptoms or diagnoses. In one embodiment, an external system template which controls an EKG machine is automatically inserted when the provider diagnoses a patient with chest pain. In another embodiment, a smoker intake workflow is automatically inserted when the provider notes a patient as a smoker. In a further embodiment, a diabetes well check workflow is inserted when the patient has been previously diagnosed with diabetes.

The present invention demonstrates significant advantages over prior art. One feature and advantage is increased EHR workflow functionality through seamless third party integration. Effectively, peripheral devices will become plug-and-play. API integration allows third party developers to provide more robust and interoperable templates and workflows with their devices. Therefore, peripheral devices will provide end users with unparalleled workflow efficiency out of the box.

Another feature and advantage is a uniform and friendly user interface. APIs and collaboratively programmed templates/workflows provide intuitive user interfaces. Further, novel use of the system's API ensures uniformity among all templates even when using third party devices thereby facilitating usability.

Still another feature and advantage is increased collaboration among system developers, end users, and third party developers. All parties collaboratively program and share EHR/EMR components. Thus, all parties can customize the EHR/EMR to meet their own needs.

Yet still another feature and advantage is automatic template injection based on symptoms or diagnoses. Providers no longer have to remember important associations between certain symptoms and actions/treatments. Thus the present invention reduces end users' malpractice liability stemming largely from the omission of mandatory treatments or procedures.

A further feature and advantage is automatic selection of pertinent workflow(s) prior to patient encounters based on chief complaints. In prior art, workflows were selected during patient encounters by the provider. Thus the present invention increases patient encounter efficiency.

BRIEF DESCRIPTION OF THE SEVERAL VIEWS OF THE DRAWINGS

The present invention will be better understood by reading the Detailed Description of the Preferred and Selected Alternate Embodiments with reference to the accompanying drawing figures, in which like reference numerals denote similar structure and refer to like elements throughout, and in which.

Figure 1:
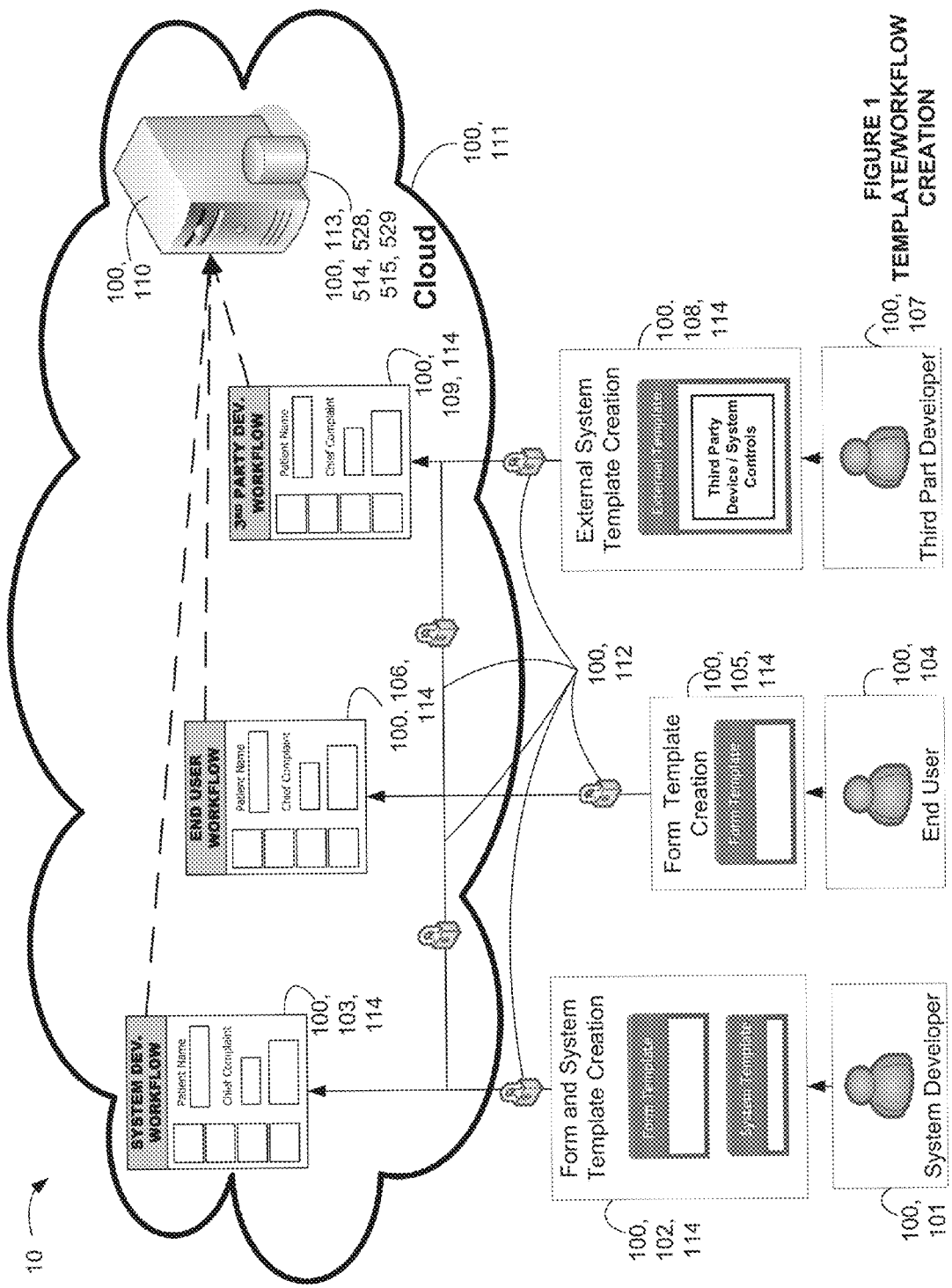
FIG. 1 is a schematic overview according to a preferred embodiment of a template/workflow creation using at least one system development workflow, at least one end user workflow and at least one third party development workflow.

It is to be noted that the drawings presented are intended solely for the purpose of illustration and that they are, therefore, neither desired nor intended to limit the invention to any or all of the exact details of the construction shown, except insofar as they may be deemed essential to the claimed invention.

DETAILED DESCRIPTION OF THE PREFERRED AND SELECTED ALTERNATE EMBODIMENTS OF THE INVENTION

In describing the preferred and selected alternate embodiments of the present invention, as illustrated in FIGS. 1-6, specific terminology is employed for the sake of clarity. The present invention, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Referring now to FIGS. 1-6, by way of example, and not limitation, there is illustrated an example embodiment of system 10 for collaborative programming of data entry workflows between system developers, end users, and third party developers, wherein system 10 comprises computer apparatus 100, patient data 404, vendor data 207 and workflow logic 405. Computer apparatus 100 comprises machine-readable medium 113, distributed computing environment 111, servers 110, display device 200, and secure communication links 112, wherein servers 110 comprise database servers 514, application servers 515, and API 302 (best shown in FIG. 5). Database servers 514 comprise databases 528 (i.e. EHR database, template database, etc.) and workflow logic 405. Workflow logic 405 comprises workflow templates 114, third party devices 401 and third party services 402 (best shown in FIG. 2 and FIG. 4). API 302 comprises hooks to database servers 514, application servers 515, and external systems or devices 501. Application servers 515 comprise applications 529 (i.e. EHR).

It will be recognized by those skilled in the art that distributed computing environment 111 may be a LAN, WAN, VPN, or any network configuration of electronic devices. It will further be recognized that application servers 515 and database servers 514 may function on separate computers (best shown in FIG. 5), or alternatively may function on the same computer (not shown). It will further be recognized that in an alternate embodiment (not shown), computer apparatus 100 may comprise a single computer that comprises both servers 110 and display device 200.

Figure 2:
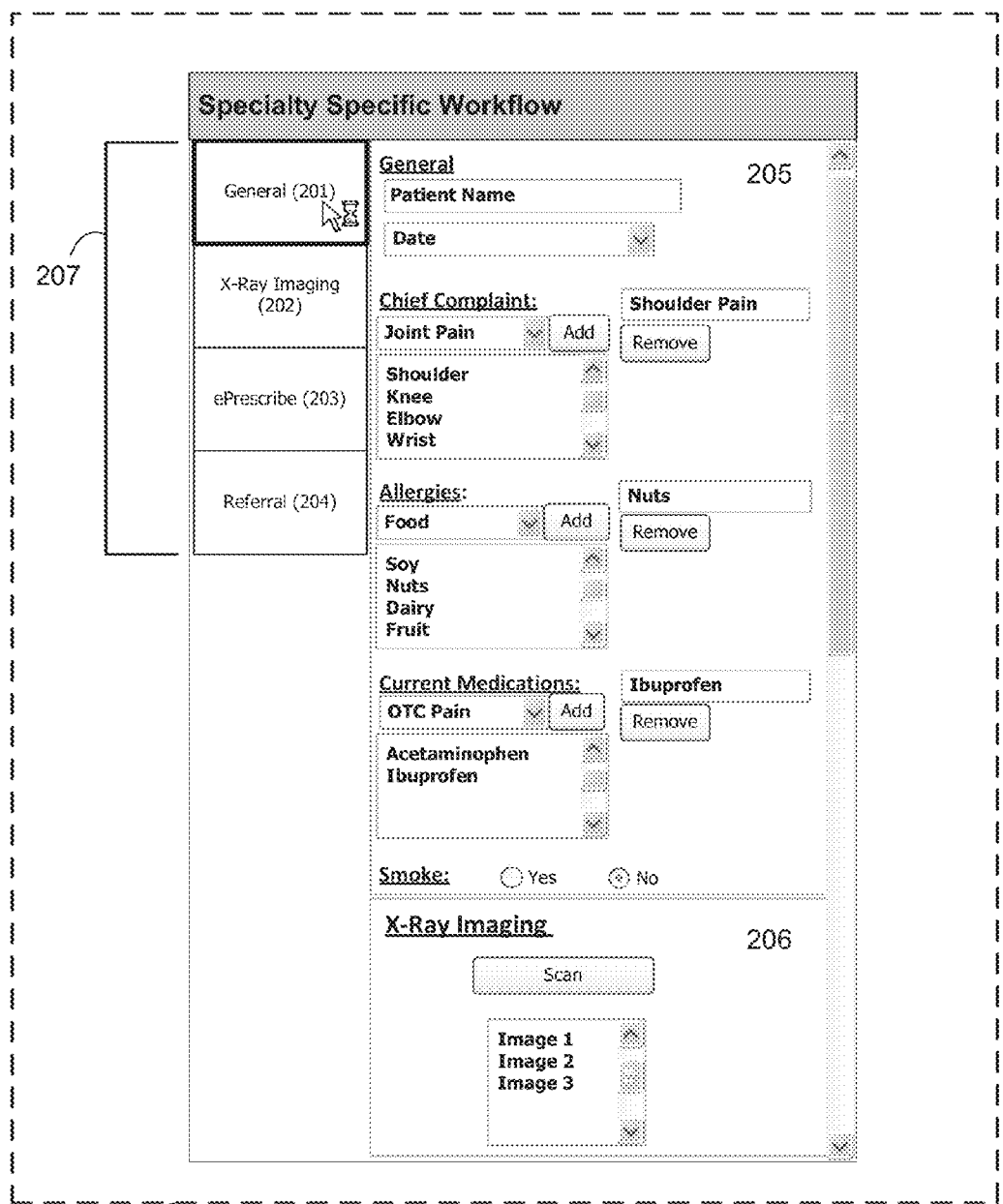
FIG. 2 is an exemplary screen shot overview of a specialty specific workflow.
Figure 3:
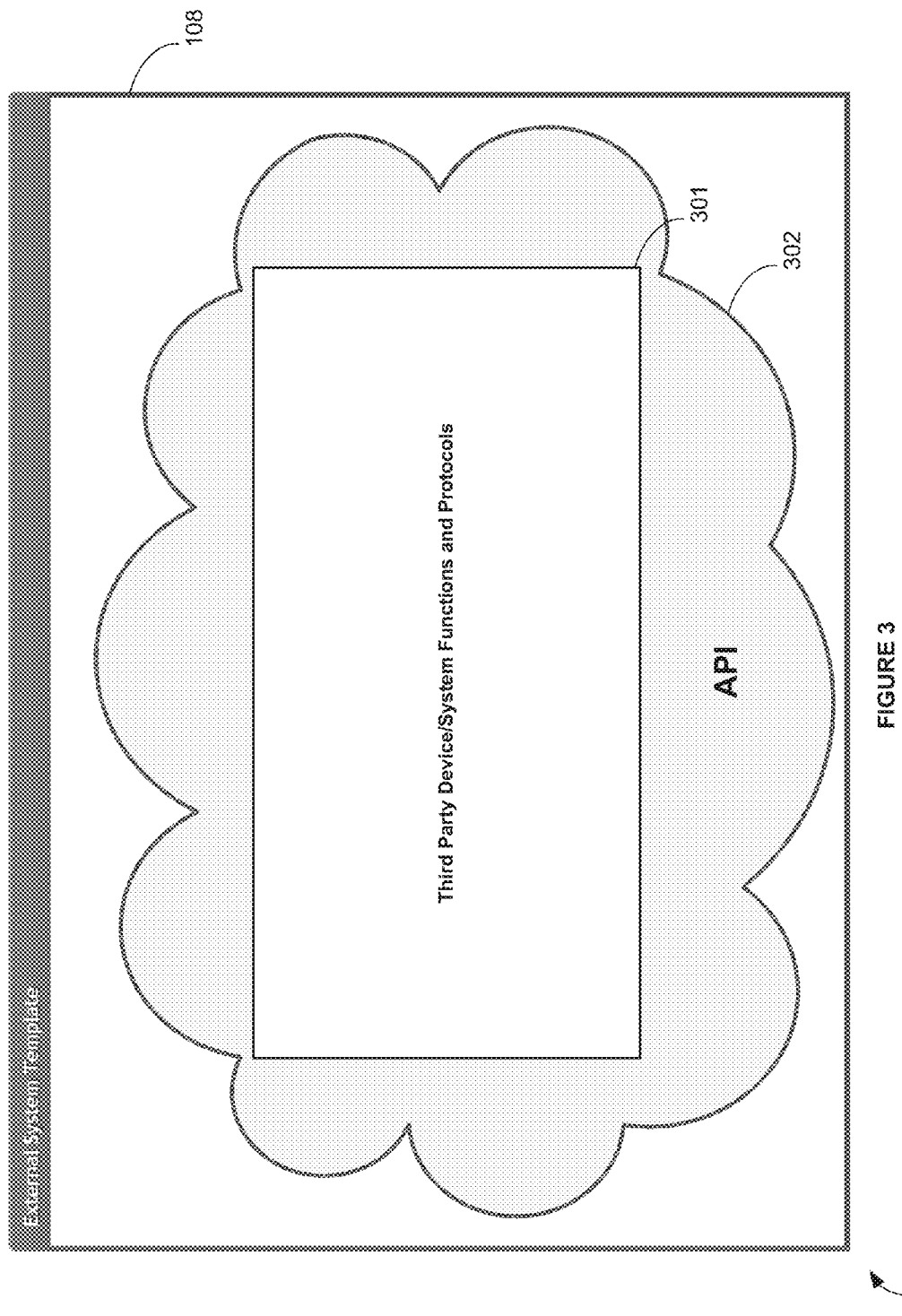
FIG. 3 is an exemplary screen shot overview of an external system template depicting the use of a proprietary API and third party device/system functions and protocols.
Figure 4:
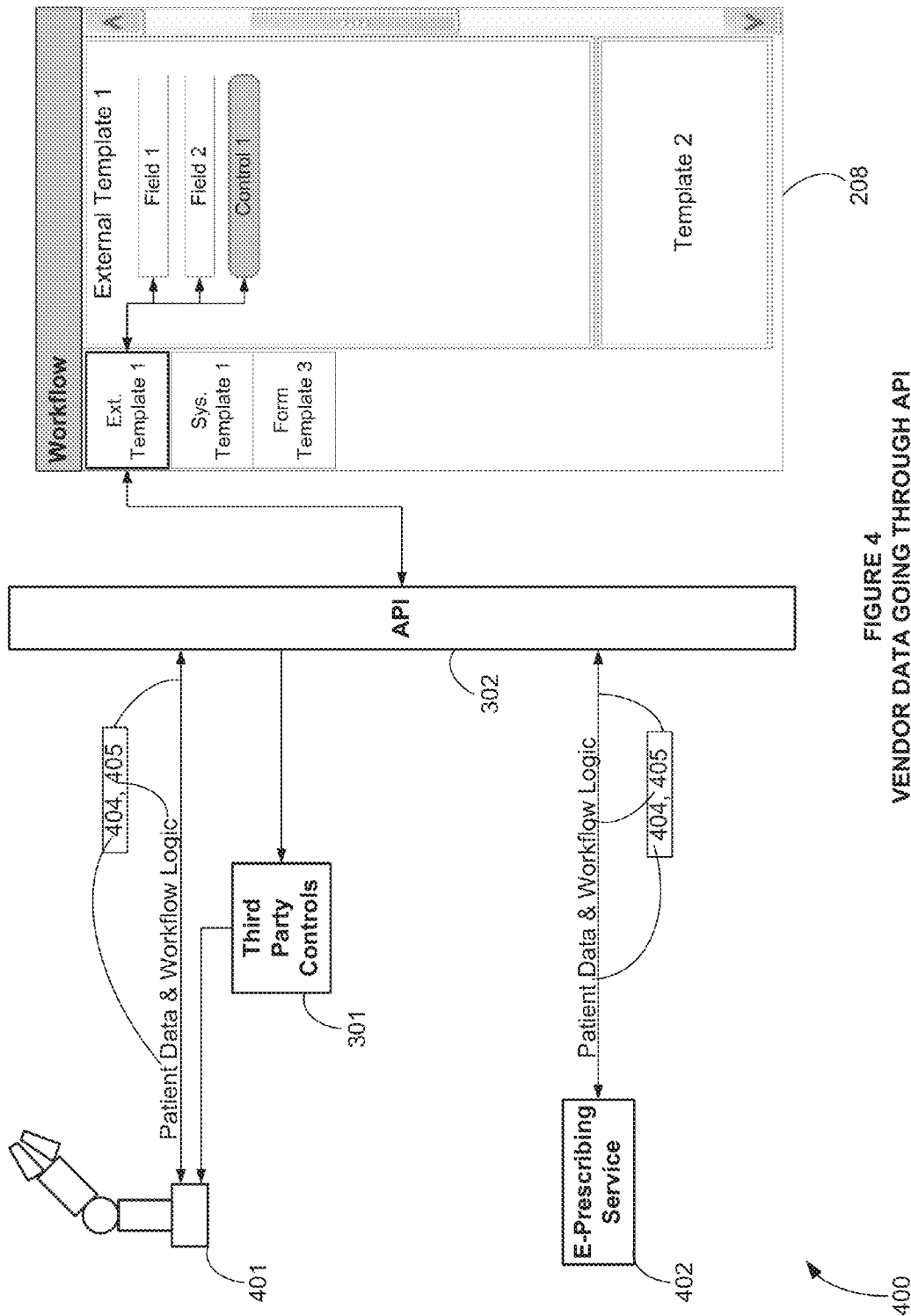
FIG. 4 is a schematic overview according to a preferred embodiment depicting an exemplary third party device and third party system connecting to the disclosed invention through a proprietary API via exemplary workflow templates.

Turning now to FIGS. 2 and 4, in use, diagnostic professional (end user 104) interacts with the display device 200, which displays the exemplary user interface 208 utilizing the workflow logic 405, wherein the end user 104 selects a specialty-specific workflow 205 depending upon the nature of the patient encounter, for example a general encounter 201, and then decides whether to create new form templates 105 comprised of additional end-user workflows 106 tailored to selections made by the end-user 104 or utilize existing form and system templates 102 comprised of system developer workflows 103 that automatically get inserted into the specialty-specific workflow 205 based on end-user activity within the workflow. The end-user 104 then inserts patient data 404 into the template(s) 105 or 102. The inserted patient data 404 then drives the workflow logic 405 and is stored in the EHR system (application 529 on application server 515 that stores in associated database 528).

Additionally, from the same specialty-specific workflow 205, the end-user 104 has the ability to interact directly with third-party services 207 and/or third-party devices 401 via third-party controls 403 via third-party developer workflows 109 comprised of external system templates 108. For example, the end-user 104 can add a third-party developer workflow for X-ray imaging 202, which utilizes third-party controls 301 that enable the X-ray device 401 to be controlled via an inserted X-ray Imaging external template 206 on the exemplary user interface 208 on the display device 200. This functionality removes other interfaces that have to be controlled separately. By using an API 302 third-party systems 401 and third-party services 402 can be seamlessly integrated, where appropriate into workflows 205 based on workflow logic 405 and patient data 404 (best shown in FIGS. 3-5).

Figure 5:
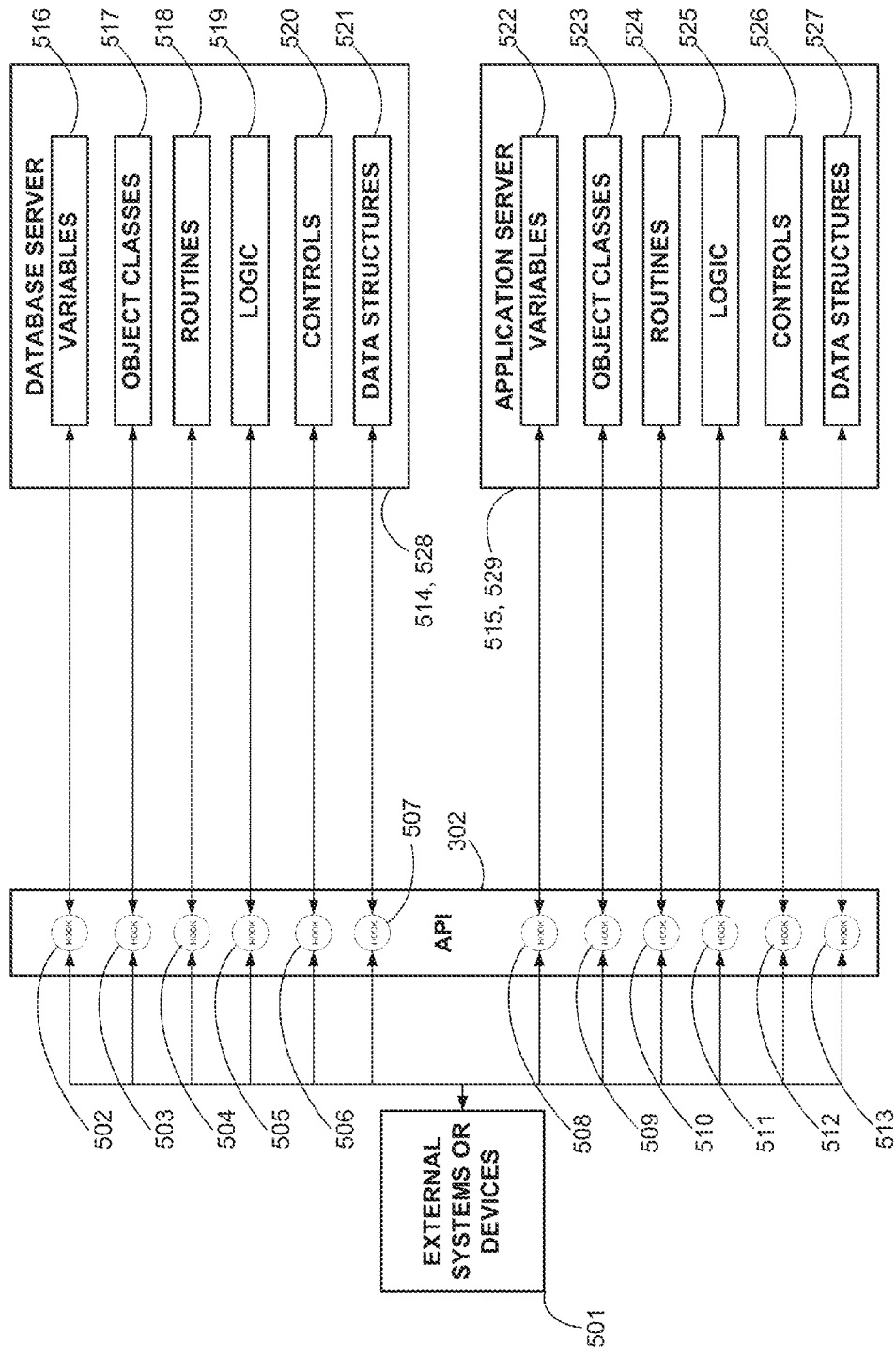
FIG. 5 is a schematic overview of an external system or device, depicting the proprietary API connections back to the present invention system.

Turning now more particularly to FIG. 5, in an exemplary embodiment of an API 302, external systems or devices 501 interact with database servers 514 and application servers 515 through the API 302. This interaction essentially makes third-party systems and devices "plug-and-play" for end-users 104, reducing complication and interface incompatibility. The database' 528 various elements (variables 516, object classes 517, routines 518, logic 519, controls 520, and data structures 521) communicate with the API 302 through associated hooks (variable hook 502, object classes hook 503, routines hook 504, logic hook 505, controls hook 506, and data structures hook 507). Likewise, the application servers' 515 various elements (variables 522, object classes 523, routines 524, logic 525, controls 526, and data structures 527) communicate with the API 302 through associated hooks (variable hook 508, object classes hook 509, routines hook 510, logic hook 511, controls hook 512, and data structures hook 513)

It will be recognized by those skilled in the art that an API 302 provides superior interoperability. Because APIs are common in the art, but also understood to reveal security vulnerabilities when fully disclosed, the lack of further disclosure herein does not represent an unwillingness to disclose, but rather an acknowledgment and a sensitivity to the careful security measures in place in an exemplary embodiment, and a recognition by those skilled in the art of the general concept and methodology of an API. Inherent in this concept and methodology is the fact that API configuration can differ substantially while still achieving the same results, depending on the system in which they are integrated.

Figure 6:
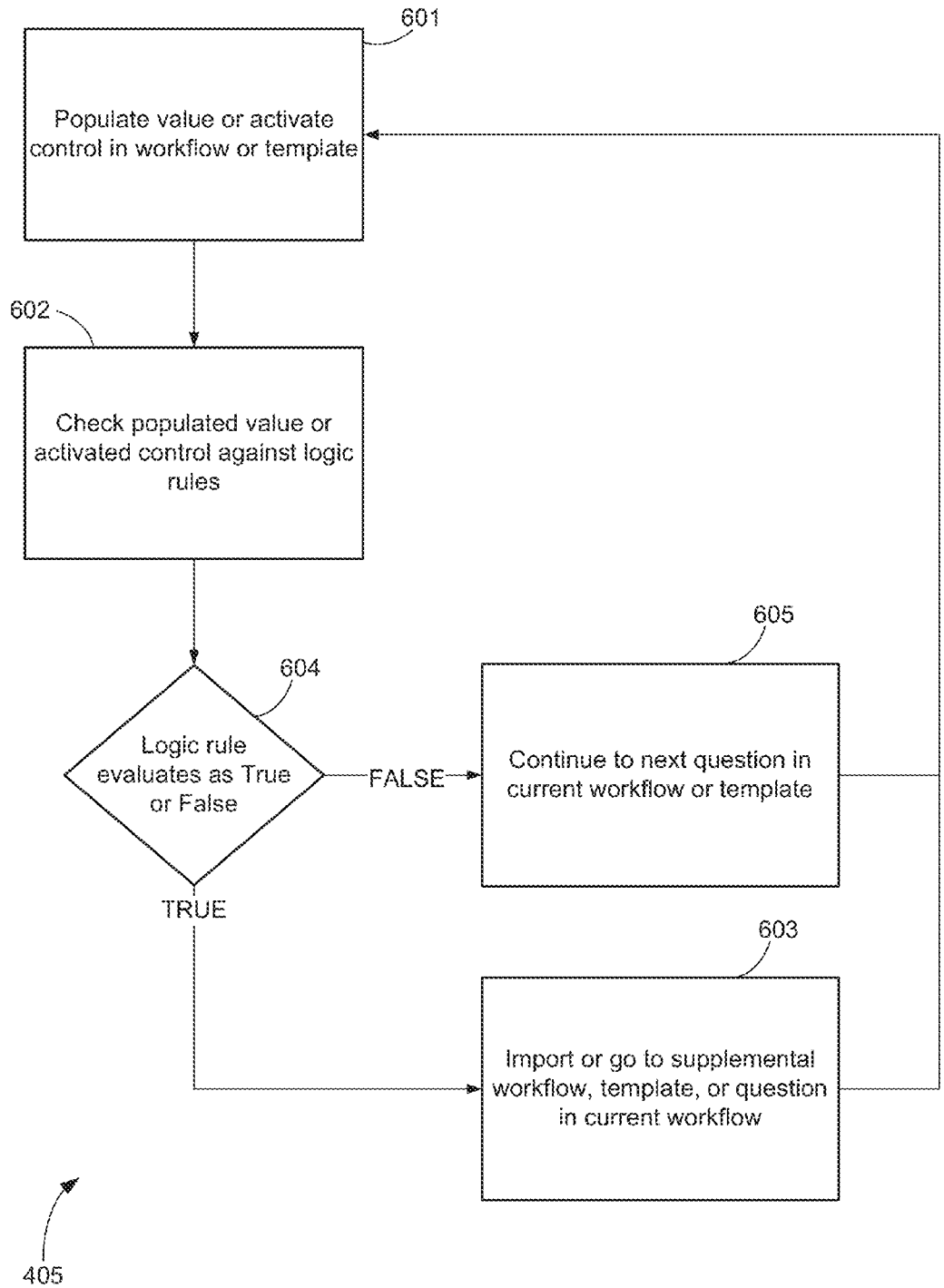
FIG. 6 is a flow chart depicting one exemplary embodiment of logic that can be used to insert elements into workflows.

Turning now to FIG. 6, the relationship between specialty-specific workflows 205 that utilize patient data 404 and the workflow logic 405 responsible for intelligently inserting additional workflows and templates into existing workflows is shown. The exemplary flow chart is a simple diagram of the decision making process included in the present invention. It will be recognized by those skilled in the art that the present invention is not intended to identify and limit itself to a single type of logic. Various types of logic can be used to achieve the same results. At step 601 the end-user 104 populates a value in a specialty-specific template 205 to activate a control in the workflow or an additional template. From there, step 602 checks the populated value or activated control against whatever logic rules have been used (i.e. branch logic, guard logic, etc.). The logic rule is then evaluated as TRUE or FALSE at step 604.

If the logic rule is evaluated as TRUE, the value or activated control is then imported into the supplemental workflow, template or question in the current workflow at step 603. On the other hand, if the logic rule is evaluated as FALSE, the value or activated control continues onto the next question in the current workflow or template at step 605. When the logic has fully evaluated the value or activated control, and has ended (i.e. in a return statement, return to control flow, etc.), the process restarts with the next value or activated control back at step 601.

The foregoing description and drawings comprise illustrative embodiments of the present invention. Having thus described exemplary embodiments of the present invention, it should be noted by those skilled in the art that the within embodiments are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions and the associated drawings. Although specific terms may be employed herein, they are used in a generic and descriptive sense only and not for purposes of limitation. Accordingly, the present invention is not limited to the specific embodiments illustrated herewith, but is limited only by the following claims.

What is claimed is:

1. A method for collaborative programming of data entry workflows, the method comprising the steps of:

accessing an application server having a processor and a memory and database server through a secure network connection, wherein said database server comprises a database;

downloading an electronic health record system stored in a memory from said application server to a networked device through said secure network connection;

creating a plurality of templates, said plurality of templates includes at least one of a form template, a system template, and an external system template, and storing said plurality of templates in said database, wherein said plurality of templates are created by at least one of an end user, a system developer, and a third party developer;

creating a plurality of workflows by arranging said plurality of templates in any order by an end user, an electronic health record system developer, and a third party developer, said plurality of workflows includes at least one of said plurality of templates configured to gather patient health information;

injecting at least one of said plurality of templates and said plurality of workflows into said electronic health record system to gather, process, and store patient health information; and integrating at least one of a plurality of peripheral devices with said plurality of workflows, wherein integration of said plurality of peripheral devices increases functionality of said networked device and electronic health record system by allowing said end user to control said peripheral devices from said networked device running the electronic health record system, and wherein said external system templates are created by said third party developer;

wherein said plurality of templates can be added in said workflows and arranged in any order by at least one of said end user, said electronic health record system developer, and said third party developer.

2. The method of claim 1, wherein said form templates further perform the step of:

capturing said patient health information via at least one data input field, and wherein said form templates are created by at least one of said end user, said electronic health record system developer, and said third party developer.

3. The method of claim 2, wherein said system templates further perform the step of:

increasing functionality of said electronic health record system by using controls and said plurality of data input fields, wherein said controls and said plurality of data input fields utilize existing functionalities of said networked device, and wherein said system templates are created by said electronic health record system developer.

4. The method of claim 3, wherein an application program interface performs the step of:

specifying at least one of a plurality of routines, a plurality of data structures, a plurality of object classes, and a plurality of variables for integration with said plurality of workflows.

5. The method of claim 3, further comprising the step of providing a plurality of peripheral devices connected to said networked device, wherein said plurality of peripheral devices communicates data to said networked device or said electronic health record system.

6. A system for collaborative programming data entry workflows, the system comprising:

an application server having a processor and a memory and a database server in a distributed computing environment;

a networked device, wherein said networked device hosts data entry workflows, a secure network connection said secure network connection exchanges data between said application server, said database server, and said networked device;

an electronic health record system stored in a memory configured to gather, process, and store patient health information in database contained in said database server, and wherein said electronic health record system is stored in said application server;

a plurality of templates, said plurality of templates includes at least one of a form template, a system template, and an external system template, and wherein said plurality of templates are stored in said database, wherein said data entry workflows includes at least one of said plurality of templates configured to gather patient health information; and a plurality of peripheral devices connected to said networked device, wherein said plurality of peripheral devices communicates data to said networked device or said electronic health record system, wherein said external system templates integrate said plurality of peripheral devices' functionalities into said workflows with an application program interface;

wherein said data entry workflows are created, modified, or deleted by an end user, an electronic health record system developer, and a third party developer by creating, modifying, or deleting said plurality of templates;

wherein said plurality of templates can be added in said workflows and arranged in any order by at least one of said end user, said electronic health record system developer, and said third party developer.

7. The system of claim 6, wherein said patient health information comprises all data collected during a patient encounter.

8. The system of claim 7, wherein said form templates comprise a series of form template data input fields, and wherein said form templates are created by at least one of said end user, said electronic health record system developer, or said third party developer.

9. The system of claim 8, wherein said system templates comprise controls and system template data input fields for advanced functionality of said electronic health record system, and wherein said system templates are created by said electronic health record system developer.

10. The system of claim 9, wherein said external system templates are created by said third party developers.

11. The system of claim 10, wherein said application program interface comprises specifications for at least one of a plurality of routines, a plurality of data structures, a plurality of object classes, and a plurality of variables for said electronic health record system.

12. The system of claim 11, wherein said plurality of peripheral devices is not created or maintained by said electronic health record system developer.

13. The system of claim 12, wherein said plurality of templates are injected into said electronic health record system where said workflows are based on said patient health information gathered in said templates.

* * * * *